United States Patent

Lorenz

[11] Patent Number: 6,150,531
[45] Date of Patent: Nov. 21, 2000

[54] BENZOXAZOLYLISOINDOLENINES

[75] Inventor: Manfred Lorenz, Köln, Germany

[73] Assignee: Bayer Aktiengesellschaft, Germany

[21] Appl. No.: 08/907,699

[22] Filed: Aug. 8, 1997

[30] Foreign Application Priority Data

Aug. 16, 1996 [DE] Germany .................. 196 32 921

[51] Int. Cl.⁷ .................................................. C07D 263/54
[52] U.S. Cl. ............................................................ 548/222
[58] Field of Search .............................................. 548/222

[56] References Cited

U.S. PATENT DOCUMENTS

| | | | |
|---|---|---|---|
| 3,794,659 | 2/1974 | Leister et al. | 548/222 |
| 5,646,290 | 7/1997 | Lorenz et al. | 548/159 |

FOREIGN PATENT DOCUMENTS

| | | |
|---|---|---|
| 0023889 | 2/1981 | European Pat. Off. . |
| 0684289 | 11/1995 | European Pat. Off. . |
| 1670748 | 5/1973 | Germany . |
| 56026898 | 8/1979 | Japan . |
| 613465 | 9/1979 | Switzerland . |

Primary Examiner—Richard L. Raymond
Assistant Examiner—Brenda Coleman
Attorney, Agent, or Firm—Conolly Bove Lodge & Hutz LLP

[57] ABSTRACT

Compounds which correspond to the formula (I) or tautomeric forms thereof

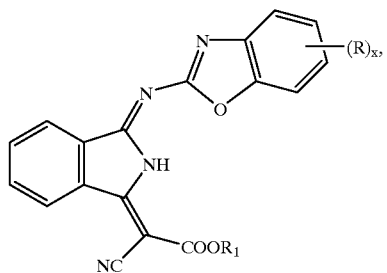

(I)

wherein $R_1$, R and x have the meaning given in the description, are particularly suitable for dyeing and printing hydrophobic synthetic or semi-synthetic materials, in particular car cover fabrics.

5 Claims, No Drawings

BENZOXAZOLYLISOINDOLENINES

The invention relates to benzoxazolylisoindolenines, a process for their preparation and their use for dyeing hydrophobic synthetic or semi-synthetic materials.

Isoindolenine dyestuffs similar to those of the formula (I) but which still have disadvantages in their use are already known from DE-A 16 70 748. Disadvantages during use are to be understood as meaning, for example, too low an affinity or build-up capacity when dyeing polyester or a poor fastness to light, in particular fastness to light when hot, such as is required if textiles dyed with these dyestuffs are used in the car sector.

Benzoxazolylisoindolenines which correspond to the formula I or tautomeric forms thereof

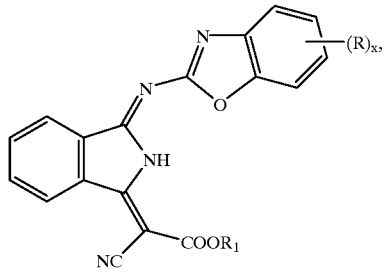

(I)

wherein $R_1$ represents a saturated or unsaturated, optionally substituted aliphatic radical having 1 to 12 carbon atoms, which is optionally interrupted by one or more oxygen atoms, an optionally substituted cycloaliphatic radical having 5 to 12 carbon atoms or an optionally substituted araliphatic radical having 7 to 20 carbon atoms, x denotes a number from 0 to 4, preferably 0, 1 or 2, and R is identical or different and represents halogen, in particular Cl or Br, $C_1$–$C_{10}$-alkyl, in particular $C_1$–$C_4$-alkyl, saturated or unsaturated $C_1$–$C_{10}$-, in particular $C_1$–$C_4$-alkoxy or -alkoxyalkoxy, CN, $NO_2$ or, if x is greater than 1, a radical of a fused-on benzene ring, have been found.

Although all the formulae described in this Application represent—where more than one is conceivable—only one tautomeric form of the particular compound(s), they are representative of all the conceivable tautomeric forms.

Furthermore, an E or Z isomer described by a formula also in each case includes, in particular in respect of the exocyclic double bond(s), the other isomer. This applies unless expressly stated otherwise.

Examples which may be mentioned of tautomeric forms of the compounds of the formula (I) are the two formulae (Ia) and (Ib)

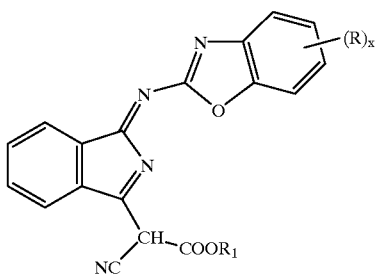

(Ia)

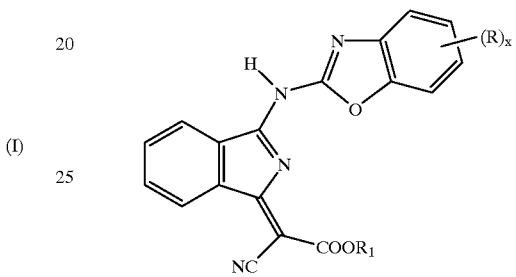

(Ib)

Examples which may be mentioned of possible substituents for the aliphatic, cycloaliphatic and araliphatic radical in $R_1$ are CN, a saturated or unsaturated oxy radical having 1 to 4 C atoms, such as $C_1$–$C_4$-alkoxy and allyloxy, and/or an acyloxy radical, such as 2-acetoxyethyl.

Suitable radicals $R_1$ are, for example: methyl, ethyl, n-propyl, allyl, n-butyl, n-pentyl, n-hexyl, n-heptyl, n-octyl, n-decyl, n-dodecyl, 2-methoxy-ethyl, 2-ethoxy-ethyl, 2-butoxy-ethyl, 3-methoxy-propyl, 3-ethoxy-propyl, 3-butoxy-propyl, 3-allyloxy-propyl, 2-ethyl-hexyl, 3-(2-ethyl-hexyloxy)-propyl, butoxyethoxy-ethyl, 2-phenoxy-ethyl, benzyl, cyclohexylmethyl, cycloheptyl, cyclopentyl and furfuryl. Possible branched radicals $R_1$ are preferably those with a methyl side chain, such as, for example: iso-butyl or iso-pentyl. Aliphatic radicals $R_1$ having 4 or more C atoms are preferred.

Preferred radicals R are chlorine, methyl, methoxy and ethoxy.

Dyestuffs of the formula (I) in which $R_1$ represents a straight-chain aliphatic radical having 4 to 8 carbon atoms, which is optionally interrupted by an oxygen atom, and R represents chlorine, methyl, methoxy or ethoxy and x denotes 0 or 1 are particularly preferred.

Especially preferred dyestuffs of the formula (I) are those in which $R_1$ represents a straight-chain aliphatic radical having 4 to 8 carbon atoms, which can also be interrupted by an oxygen atom, and x represents 0.

The invention furthermore relates to a process for the preparation of compounds of the formula (I), which is characterized in that either a compound of the formula (II) is subjected to a condensation reaction with a cyanoacetic acid ester of the formula (III) according to the equation

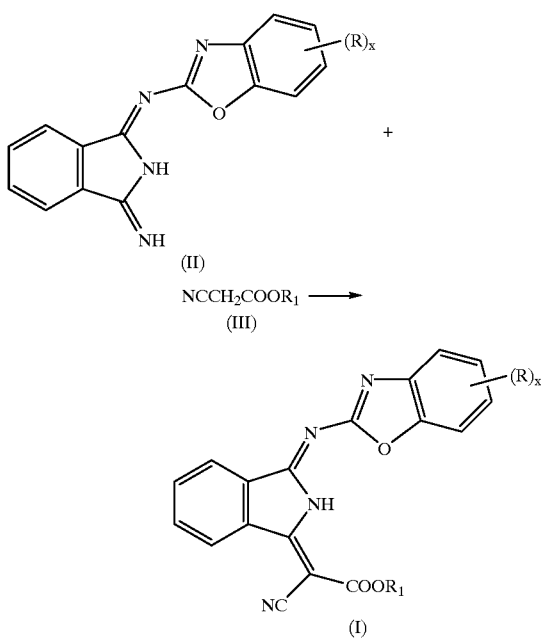

or a compound of the formula (IV) is subjected to a condensation reaction with 2-amino-benzoxazoles of the formula (V) according to the equation

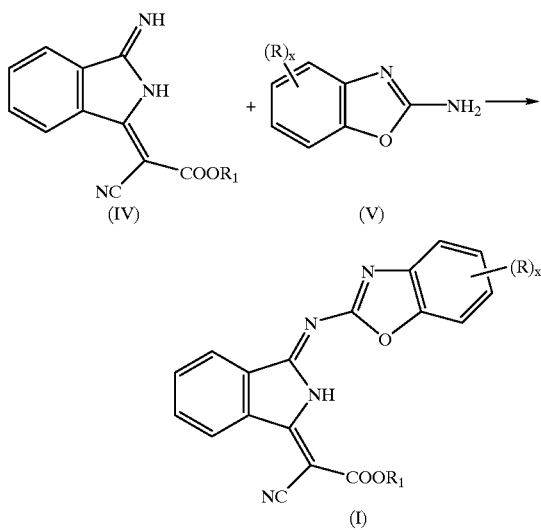

wherein

R, $R_1$ and x have the abovementioned meaning.

In each case one equivalent of ammonia is liberated during the reactions.

Compounds of the formula (IV) are already known from DE-A-16 70 748 which corresponds to U.S. Pat. Nos. 3,646,033 and 3,794,659.

The process according to the invention is particularly preferably carried out by reaction of compounds of the formula (II) with those of the formula (III).

The reaction of (II) with (III) or (IV) with (V), particularly preferably (II) with (III), is preferably carried out in water, in organic, preferably polar organic solvents, or in mixtures thereof.

Examples of polar organic solvents which may be mentioned are: amides, such as dimethylformamide, formamide, dimethylacetamide and N-methylpyrrolidone, and furthermore dimethyl sulphoxide, acetonitrile or acetic acid. In a preferred embodiment, the reaction is carried out in an alcohol on which the radical $R_1$ is based. These solvents can be employed by themselves or as a mixture.

The process according to the invention is preferably carried out at reaction temperatures of 50 to 150° C., in particular 60 to 100° C. Components (II) and (III) can be employed in equivalent amounts or one of them can be employed in excess, an excess of cyanoacetic acid ester of 5 to 50%, preferably 5 to 30%, being advantageous, since it has been found, surprisingly, that this leads to particularly short reaction times and to very pure end products.

When carrying out the present invention, it has been found, surprisingly, that water or an aqueous medium can also be particularly advantageously used as the reaction medium for the reaction of compounds of the formula (II) with compounds of the formula (III) according to the above equation. In addition to water, organic solvents can also be present, and in particular preferably those which are completely or partly miscible with water, such as, for example, alcohols, preferably the alcohols on which the radical $R_1$ is based, ketones, such as, for example, acetone, methyl ethyl ketone and cyclohexanone, ethers, such as tetrahydrofuran and dioxane, dimethylformamide, N-methylpyrrolidone and the like. However, water-immiscible solvents can also be added, for example in order to improve the crystallinity and to achieve particular crystal forms. These solvents can be present from the beginning or can alternatively be added only in the course of the reaction.

In a particularly preferred embodiment of the process according to the invention, the reaction is carried out in the presence of an organic acid. This as a rule leads to an acceleration of the reaction, higher yields and a higher purity often also being achieved. Suitable organic acids are, for example, lower aliphatic, saturated or unsaturated mono- or dicarboxylic acids, such as, for example, formic acid, acetic acid, propionic acid, butyric acid, oxalic acid, fumaric acid, maleic acid, succinic acid, glutaric acid and adipic acid, and also aromatic acids, such as, for example, benzoic acid, phthalic acid, phenylacetic acid and iso- and terephthalic acid. The acids are preferably added in amounts of 0.2 to 3 equivalents, preferably 1 to 2 equivalents, based on the components II, III, IV or V. However, higher amounts of acid can also be employed, preferably if the acid simultaneously serves as the solvent, for example acetic acid.

If water or a predominantly aqueous medium is used as the reaction medium, it is advantageous to add surface-active substances, such as surfactants, dispersing agents, emulsifiers and wetting agents. The known non-ionic, anionic and cationic auxiliaries are possible. Such compounds are, for example, salts of alkylbenzenesulphonic acids, alkylphenolsulphonic acids and alkylnaphthalenesulphonic acids, condensation products of phenolsulphonic acids, formaldehyde and urea, ligninsulphonates and addition products of ethylene oxide and propylene oxide on alkanols, alkanediols, phenols, carboxylic acids, amines, carboxylic acid amides and their sulphuric acid half-esters, it also being possible for mixtures of these compounds to be employed. However, ligninsulphonates, such as, for example, kraft lignins of the Reax® type from Westvaco or sulphite lignins of the Ufoxane® type from Borregaard, are particularly preferred.

The compounds of the formula (IV) are preferably obtained by reaction of aminoiminoisoindolenine of the formula (VI) with a cyanoacetic ester of the formula (III)

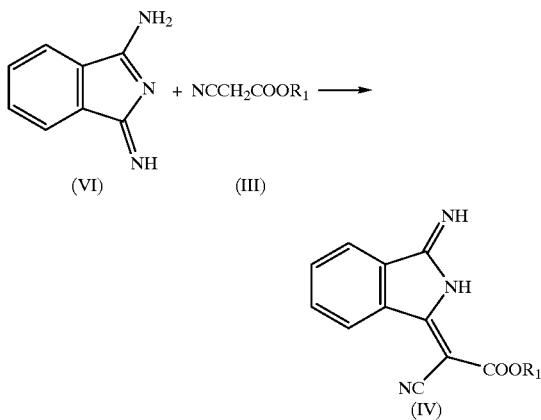

and the compounds of the formula (II) are preferably obtained by reaction of aminoiminoisoindolenine (VI) with 2-aminobenzoxazoles of the formula (V)

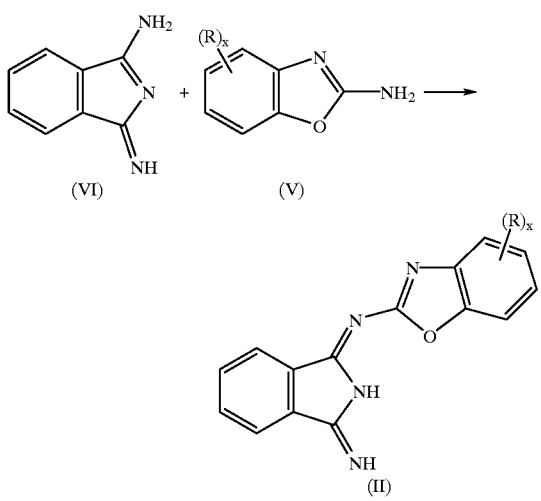

wherein

R, $R_1$ and x have the abovementioned meanings.

The preparation of the monocondensates (IV) and (II) is preferably carried out by heating components VI and III or VI and V in water, an organic solvent or mixtures thereof, possible solvents being the solvents already mentioned above, in particular amides, for example formamide, dimethylformamide, dimethylacetamide and N-methylpyrrolidone, and preferably alcohols, in particular lower alcohols, such as methanol, ethanol, n-propanol and isopropanol. Organic acids, which in general accelerate the reaction, are also advantageously added for the preparation of the monocondensates. The same acids as have already been described above are possible for this. An addition of aliphatic amines as a rule also has an accelerating action, cycloaliphatic amines being particularly suitable. Such amines are, for example, piperidine, piperazine or morpholine.

It is advantageous to carry out the reaction of VI and III in water or in an aqueous medium, such as is described for the reaction of II with III, and to carry out the reaction of VI and V in an organic solvent.

The process according to the invention for the preparation of the compound of the formula (I) is particularly preferably characterized in that the monocondensates (II) and (IV) prepared as described above are not intermediately isolated and the reaction is carried out starting from aminoiminoisoindolenine of the formula (VI).

The invention furthermore relates to a process for the preparation of compounds of the formula (II), which is characterized in that compounds of the formula (VIIa) and/or (VIIb) are reacted with 2-amino-benzoxazoles of the formula (V)

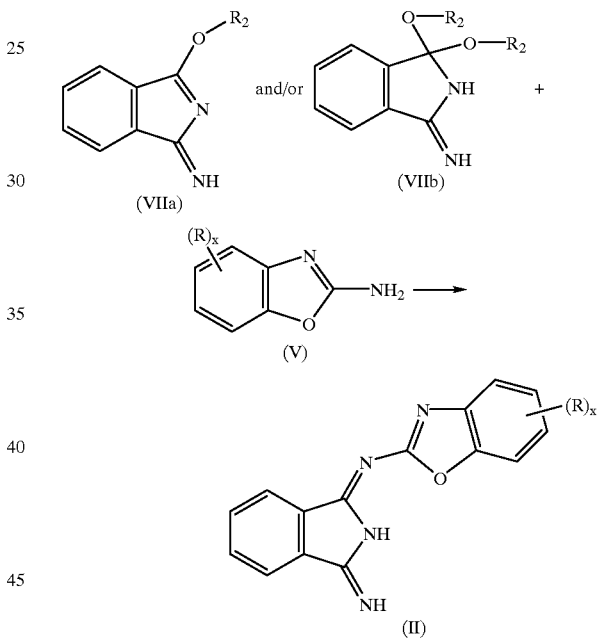

wherein

R and x have the abovementioned meaning and $R_2$ represents an aliphatic radical, in particular $C_1$–$C_4$-alkyl.

Compounds of the formula (VIIa) and (VIIb) are known, for example, from DE-A-16 70 748 which corresponds to U.S. Pat. Nos. 3,646,033 and 3,794,659. They are preferably prepared by reaction of phthalic acid dinitrile with aliphatic $C_1$–$C_4$-alcohols according to the following equation:

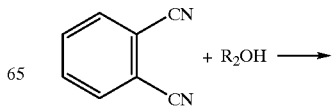

-continued

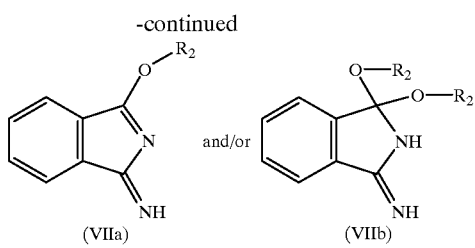

(VIIa) and/or (VIIb)

wherein

R$_2$ has the abovementioned meaning.

The compounds R$_2$OH are, in particular, alcohols, such as, for example, methanol, ethanol, propanol and isopropanol, preferably methanol. The reaction of (VIIa) and/or (VIIb) with (V) is preferably carried out without intermediate isolation of the compounds (VIIa) or (VIIb), with addition of the corresponding 2-amino-benzoxazoles (V) and heating until no further compound (VIIa) or (VIIb) is detectable. The reaction temperatures both for the preparation of (VIIa) or (VIIb) and for (II) are preferably between 20 and 80° C.

Compounds of the formula (VIIa) and (VIIb) are preferably prepared in the presence of a base, preferably in the presence of an alcoholate, in particular R$_2$OMe, wherein Me denotes an alkali metal, such as Na, K or Li, and R$_2$ has the abovementioned meaning.

When the reaction has ended, the alcoholate, which serves as a catalyst, is preferably neutralized with an acid, for example with acetic acid, and the product which has precipitated out is then isolated or, after dilution with a solvent, further reacted directly, it being possible for the solvents already mentioned to be used.

The invention furthermore relates to compounds of the formula (II)

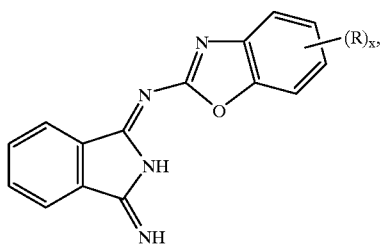

(II)

wherein

R and x have the abovementioned meaning.

The invention furthermore relates to the use of dyestuffs of the formulae (I) for dyeing fully synthetic or high molecular weight substances. They are particularly suitable for dyeing or printing synthetic fibre materials of aromatic polyesters and/or cellulose acetates. They have a high tinctorial strength and show an out-standing fastness to light, in particular a high fastness to light when hot, and are therefore particularly suitable for dyeing and printing textile materials for cars and for dyeing so-called microfibres. They are also suitable for so-called thermo-transfer printing on textile and non-textile substrates, for example by the D2T2 (dye diffusion thermo transfer) process for recording images. The dyestuffs can furthermore be used for bulk dyeing of plastics, for example of polyethylene, polypropylene, styrene and polycarbonates, and of blends of plastics, such as, for example, ABS. The dyestuffs are fluorescent in some cases and are therefore also suitable as fluorescent dyestuffs.

Textile materials of polyester can be dyed with the dyestuffs according to the invention by a type of spin dyeing, but are preferably dyed from aqueous suspension. For this, the dyestuffs are processed to form dye preparations in the generally customary manner, for example by grinding in water in the presence of dispersing and/or filling agents. Using the preparations, which are dried in vacuo or by atomizing, if appropriate, dyeing, padding or printing can be carried out in a so-called short or long liquor, after addition of water.

To establish or improve the degree of dispersion, a surface-active agent or a mixture of such auxiliaries can be added during grinding or during the synthesis reaction. The particle size of the dyestuff particles can of course be influenced accordingly and brought to a required value by a grinding treatment, for example wet bead grinding, either during the synthesis or thereafter.

Possible dispersing agents are those of an anionic or non-anionic nature. In addition to dispersing agents of one or other of the groups, it is also possible to employ dispersing agent mixtures, mixtures of non-ionic and anionic dispersing agents primarily being intended, since anionic and cationic dispersing agents tend to form precipitates when mixed with one another.

In the case of anionic dispersing agents, condensation products of aromatic sulphonic acids and formaldehyde, such as condensation products of formaldehyde and alkylnaphthalenesulphonic acids, or of formaldehyde, naphthalenesulphonic acids and benzenesulphonic acid, and condensation products of optionally substituted phenol with formaldehyde and sodium bisulphite have proved to be effective in particular.

Ligninsulphonates, for example those which are obtained by the sulphite or kraft process, are furthermore possible above all. These are preferably products which are partly hydrolysed, oxidized, propoxylated or desulphonated, and fractionated by known processes, for example according to the molecular weight or the degree of sulphonation. Mixtures of sulphite ligninsulphonates and kraft ligninsulphonates also have a good action.

Ligninsulphonates having an average molecular weight of between 1,000 and 100,000, a content of active ligninsulphonate of at least 80% and, preferably, a low content of polyvalent cations are particularly suitable. The degree of sulphonation can vary within wide limits.

Non-ionic dispersing agents or emulsifiers are, for example, reaction products of alkylene oxides with alkylatable compounds, such as, for example, fatty alcohols, fatty amines, fatty acids, phenols, alkylphenols, arylalkylphenols and carboxylic acid amides.

These are, for example, ethylene oxide adducts from the class of reaction products of ethylene oxide with:
a) saturated and/or unsaturated fatty alcohols having 6 to 20 C atoms; or
b) alkylphenols having 4 to 12 C atoms in the alkyl radical, or
c) saturated and/or unsaturated fatty amines having 14 to 20 C atoms or d) saturated and/or unsaturated fatty acids having 14 to 20 C atoms.

Ethylene oxide adducts which may be mentioned specifically are:

a) reaction products of saturated and/or unsaturated fatty alcohols having 6 to 20 C atoms with 5 to 30 mol of ethylene oxide
b) reaction products of alkylphenols having 4 to 12 C atoms with 5 to 20 mol of ethylene oxide
c) reaction products of saturated and/or unsaturated fatty amines having 14 to 20 C atoms with 5 to 20 mol of ethylene oxide
d) reaction products of saturated and/or unsaturated fatty acids having 14 to 20 C atoms with 5 to 20 mol of ethylene oxide.

Further preferred dispersing agents are alkoxylated styrene-phenol condensation products, which are optionally employed as a mixture with their inorganic esters, which are obtained by reaction of the alkoxylated styrene-phenol condensation product with inorganic acids, such as, for example, amidosulphonic acid.

Mixtures of dyestuffs of the formula (I) are also particularly suitable for dyeing polyester, whereby, under certain circumstances, the affinity and build-up capacity of the dyestuffs and their dispersibility can be improved.

The new dyestuff mixtures can be prepared by various processes:

1. by mixing the separately prepared and finished individual dyestuff components,
2. by finishing the separately prepared individual components together,
3. by synthesis of mixtures of the dyestuffs of the formula (I) together from mixtures of different precursors.

The dyestuffs are expediently mixed in suitable mills, for example bead or sand mills. However, separately finished individual dyestuffs can also be mixed by stirring into dye liquors.

Mixtures of dyestuffs of the formula (I) which differ only in terms of the radical $R_1$ are particularly suitable.

However, the dyestuffs are also outstandingly suitable for the preparation of mixtures with other disperse dyestuffs to produce, for example, brown, grey or green shades on the fibre, because they do not impair the fastness of these dyestuffs to light.

Another preferred embodiment of the present invention relates to mixtures of one or more of the dyestuffs of the formula (I) with one or more dyestuffs such as are usually used for dyeing polyester fibres or polyester textile materials for car cover fabrics. These dyestuffs for dyeing car cover fabrics can be, in particular, azo, disazo, anthraquinone, nitro, naphthalimide and terephthalimide dyestuffs. Particularly preferred dyestuffs for such mixtures are, for example, the Colour Index dyestuffs Yellow 23, 42, 51, 59, 65, 71, 86, 108, 122, 163, 182, 211, Orange 29, 30, 32, 41, 44, 45, 61, 73, Red 60, 82, 86, 91, 92, 127, 134, 138, 159, 167, 191, 202, 258, 279, 284, 302, 323, Blue 27, 54, 56, 60, 73, 77, 79, 79:1, 87, 266, 333, 361 and Violet 27, 28, 57, 95, the weight ratios of the dyestuff mixtures depending on the desired colour shade.

EXAMPLES

Example 1

86.1 g (0.55 mol) of technical grade aminoiminoisoindolenine (92.8% pure), 67 g of 2-aminobenzoxazole and 5 g of piperazine were stirred with 500 ml of methanol and the mixture was heated under reflux for 5 hours. Thereafter, the batch was cooled to room temperature and, after dropwise addition of 200 ml of water, the product which had precipitated out was filtered off with suction and washed with water. After drying, 87.9 g of a product of the formula

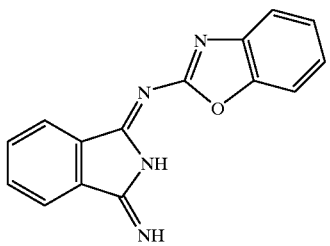

were obtained. The product was purified further by recrystallization from dimethylformamide.

Elemental analysis: $C_{15}H_{10}N_4O$; molecular weight=262.3 g/mol

|  | C | H | N |
|---|---|---|---|
| calculated: | 68.7 | 3.8 | 21.4 |
| found: | 68.9 | 3.6 | 21.1 |

Example 2

54.9 g of phthalic acid dinitrile were added to a mixture of 80 ml of methanol and 80 ml of a 30% strength sodium methylate solution in the course of 30 minutes, during which the temperature was kept at 20–25° C. by gentle cooling. Thereafter, 53.6 g of 2-aminobenzoxazole were sprinkled in over a period of about 15 minutes, and the batch was subsequently stirred at room temperature for a further 5 hours. It was then heated at 40° C. for a further 15 minutes, 25 ml of glacial acetic acid were added dropwise and the mixture was kept at 60° C. for a further 30 minutes. The product which precipitated out was filtered off with suction at room temperature and washed with water and methanol. 84.8 g of a product of the same formula as in Example 1 were obtained.

Example 3

26.2 g (0.1 mol) of the substance from Example 2 and 300 ml of amyl alcohol were stirred, and 17 g (0.11 mol) of amyl cyanoacetate and 6 ml of glacial acetic acid were added. The batch was heated at 80° C. for 3 hours and then briefly at 100° C. After cooling to room temperature, the substance which had precipitated out was filtered off with suction and washed with ice-cold methanol and with water. After drying, 29.2 g of a product of the following formula

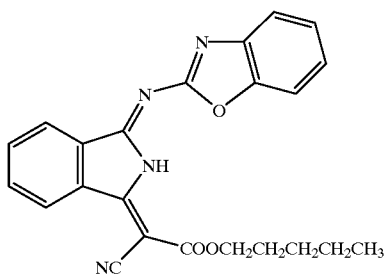

were obtained. The dyestuff dyes polyester fibres in greenish-tinged yellow shades with outstanding fastness to light.

Example 4

26.2 g (0.1 mol) of the substance from Example 2, 150 ml of water and 2.4 g of Lignisol® SD 60, a dispersing agent based on ligninsulphonates from Borregaard, were stirred, 6 ml of glacial acetic acid were added and the mixture was heated up to 70° C. Thereafter, 17.1 g of amyl cyanoacetate were added dropwise in the course of 30 minutes and the mixture was heated to 90° C. and the temperature maintained for 5 hours. The product which had precipitated out was filtered off with suction at room temperature and washed with water and methanol. 36.5 g of the same dyestuff as in Example 3 were obtained.

Example 5

If the procedure was as in Example 4, but butylglycol cyanoacetate was employed instead of amyl cyanoacetate, a dyestuff of the formula:

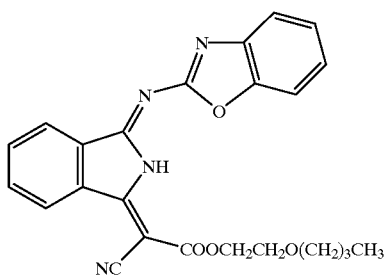

was obtained in a comparable yield. The dyestuff has properties similar to those of the dyestuff of Example 4, but has an even somewhat better fastness to light and an even better fastness to sublimation.

If the procedure was as in Examples 1–5 and the corresponding cyanoacetic acid esters and 2-amino-benzoxazoles were employed in these in an analogous manner, the dyestuffs listed in Table 1 below were obtained.

TABLE 1

(Unless stated otherwise, $R_3$ and $R_4$ in the table represent hydrogen)

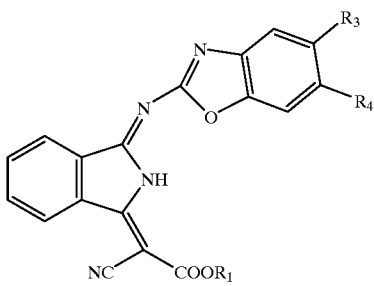

| Example No. | $R_1$ | $R_4$ | $R_3$ | Colour change |
|---|---|---|---|---|
| 6 | n-Hexyl | | | greenish yellow |
| 7 | n-Octyl | | | greenish yellow |
| 8 | n-Nonyl | | | greenish yellow |
| 9 | —CH$_2$CH$_2$OCH$_3$ | | | greenish yellow |
| 10 | —CH$_2$CH$_2$OCH$_2$CH$_3$ | | | greenish yellow |
| 11 | —CH$_2$CH$_2$OCH(CH$_3$)$_2$ | | | greenish yellow |
| 12 | Benzyl | | | greenish yellow |
| 13 | Phenylethyl | | | greenish yellow |
| 14 | Furfuryl | | | greenish yellow |
| 15 | n-Butyl | CH$_3$ | | yellow |
| 16 | n-Hexyl | CH$_3$ | | yellow |
| 17 | —CH$_2$CH$_2$O(CH$_2$)$_3$CH$_3$ | CH$_3$ | | yellow |
| 18 | n-Amyl | | CH$_3$ | yellow |
| 19 | —CH$_2$CH$_2$O(CH$_2$)$_3$CH$_3$ | | CH$_3$ | yellow |
| 20 | n-Hexyl | | CH$_3$ | yellow |
| 21 | Cyclohexylmethyl | | CH$_3$ | yellow |
| 22 | —CH$_2$CH$_2$OCH$_2$CH$_3$ | | CH$_3$ | yellow |
| 23 | n-Amyl | | Cl | greenish yellow |
| 24 | n-Hexyl | | Cl | greenish yellow |
| 25 | Benzyl | | Cl | greenish yellow |
| 26 | Cyclohexylmethyl | | Cl | greenish yellow |
| 27 | —CH$_2$CH$_2$O(CH$_2$)$_3$CH$_3$ | | Cl | greenish yellow |

Finishing Example 1

55 g of ligninsulphonate, Na salt and 5 g of a non-ionic dispersing agent (addition product of abietic acid and 50 molar equivalents of ethylene oxide) were added to 26 g of the dyestuff obtained in Example 5 (in the form of the water-moist press-cake) in 200 ml of water, and the pH was brought to 7 with sulphuric acid. The mixture was then ground at room temperature in a bead mill for 1 hour, until finely divided (90%≦$\mu$m), sieved and dried in a spray drier.

Finishing Example 2

The procedure was as in Finishing Example 1, but the 5 g of non-ionic dispersing agent were replaced by 5 g of a surfactant mixture based on an alkoxylated styrene-phenol condensation product (phenol/styrene=2.8:1, 29 molar equivalents of ethylene oxide) and an inorganic ester thereof (amidosulphonic acid), which additionally comprises a condensation product of oleic acid and 6.5 molar equivalents of ethylene oxide.

Use Example 1

2 g of the powder obtained according to Finishing Example 1 were dispersed in 1,000 g of water. 0.5 to 2 g/l of a commercially available dispersing agent based on a condensation product of naphthalenesulphonic acid sodium salt and formaldehyde, 0.5 to 2 g/l of monosodium phosphate and 2 g of a commercially available levelling auxiliary were added to the dispersion and the pH was brought to 4.5 to 5.5 with acetic acid. 100 g of a texturized polyester fabric based on polyethylene glycol terephthalate were introduced into the dye liquor thus obtained and dyeing was carried out at 130° C. for 60 minutes.

Use Example 2

The dyestuff preparation obtained according to Finishing Example 2 was also used for dyeing in an analogous manner to Example 1.

Deep brilliant yellow dyeings with outstanding coloristic properties, such as fastness to light, were obtained, the heat stability of the dyestuff dispersion and the levelness of the dyeing from Use Example 2 being improved further.

What is claimed is:

1. A compound which correspond to the formula (I) or a tautomeric form thereof

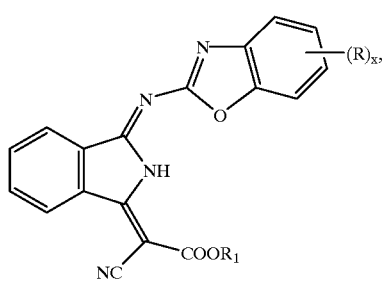

(I)

wherein $R_1$ represents a saturated or unsaturated, substituted or unsubstituted aliphatic radical having 1 to 12 C atoms, which is uninterrupted or interrupted by one or more oxygen atoms, an unsubstituted or substituted cycloaliphatic radical having 5 to 12 C atoms or an unsubstituted or substituted araliphatic radical having 7 to 20 C atoms, x denotes a number from 0 to 4 and R is identical or different and represents halogen, $C_1$–$C_{10}$-alkyl, saturated or unsaturated $C_1$–$C_{10}$-alkoxy or -alkoxyalkoxy, CN, $NO_2$ or, if x is greater than 1, the radical of a fused-on benzene ring.

2. The compound according to claim 1, wherein

R is identical or different and represents Cl, Br, $C_1$–$C_4$-alkyl, saturated or unsaturated $C_1$–$C_4$-alkoxy or -alkoxyalkoxy, CN, $NO_2$ or, if x is greater than 1, the radical of a fused-on benzene ring.

3. The compound according to claim 1, wherein $R_1$ represents a straight-chain aliphatic radical having 4 to 8 C atoms, which is uninterrupted or interrupted by an oxygen atom, and R represents Cl, methyl, methoxy or ethoxy and x represents 0 or 1.

4. The compound according to claim 1, wherein x denotes 0.

5. The compound according to claim 1, wherein x denotes 0, 1 or 2.

* * * * *